(12) United States Patent
Fernando et al.

(10) Patent No.: US 9,580,660 B2
(45) Date of Patent: Feb. 28, 2017

(54) DEOXYGENATION OF BIOMASS DERIVED OXYGENATES TO HYDROCARBONS VIA DIRECT METHANE INTERVENTION

(75) Inventors: Sandun Fernando, College Station, TX (US); Duminda Anuradh Gunawardena, College Station, TX (US)

(73) Assignee: The Texas A&M University System, College Station, TX (US)

( * ) Notice: Subject to any disclaimer, the term of this patent is extended or adjusted under 35 U.S.C. 154(b) by 969 days.

(21) Appl. No.: 13/157,455

(22) Filed: Jun. 10, 2011

(65) Prior Publication Data
US 2011/0313219 A1    Dec. 22, 2011

Related U.S. Application Data

(60) Provisional application No. 61/356,303, filed on Jun. 18, 2010.

(51) Int. Cl.
*C10G 3/00* (2006.01)
*C07C 2/76* (2006.01)
(Continued)

(52) U.S. Cl.
CPC .............. *C10G 3/49* (2013.01); *C07C 2/76* (2013.01); *C10G 1/002* (2013.01); *C10G 3/44* (2013.01);
(Continued)

(58) Field of Classification Search
CPC ... C10G 1/00; C10G 3/00; C10G 3/42; C10G 3/50; C10G 3/52; C10G 3/49;
(Continued)

(56) References Cited

U.S. PATENT DOCUMENTS

| 3,894,107 A | 7/1975 | Butter et al. .................. 585/408 |
| 4,549,031 A | 10/1985 | Chen et al. .................. 585/408 |

(Continued)

OTHER PUBLICATIONS

"Glucose." Encyclopaedia Britannica. Encyclopaedia Britannica Online Academic Edition. Encyclopædia Britannica Inc., 2014. Web. Aug. 4, 2014. <http://www.britannica.com/EBchecked/topic/235853/glucose>.*

(Continued)

*Primary Examiner* — In Suk Bullock
*Assistant Examiner* — Philip Louie
(74) *Attorney, Agent, or Firm* — Medlen and Carroll, LLP (57) ABSTRACT

The application describes a process where methane or any short chained hydrocarbon could be catalytically coupled with an oxygenate (preferably derived from thermal processing of biomass) to dehydrate and produce a deoxygenated hydrocarbon. The presence of oxygen in biomass derivatives adversely affects its ability to be further processed into hydrocarbon fuels because the resulting water poisons many catalysts (including alumina containing catalysts, zeolites, etc.) found in petrochemical refineries. While commonly used hydrodeoxygenation methods require expensive hydrogen to instigate deoxygenation, the present process uses short chained hydrocarbons (such as methane or natural gas) to instigate hydrodeoxygenation.

9 Claims, 11 Drawing Sheets

Metal impregnated ZSM-5

Methane Steam Reforming

Biomass Oxygenates Dehydrative Aromatization $$CH_4 + H_2O \rightarrow H_2 + CO_2$$

$$C_xH_yO_z + H_2 \rightarrow BTEX + H_2O$$

Overall: $C_xH_yO_z + CH_4 \rightarrow BTEX + CO_2$ (51) Int. Cl.
 C10G 1/00 (2006.01)
 C10G 45/30 (2006.01)
(52) U.S. Cl.
 CPC .............. C10G 3/47 (2013.01); C10G 3/52 (2013.01); C10G 45/30 (2013.01); C07C 2529/40 (2013.01); C10G 2300/1014 (2013.01); C10G 2300/1025 (2013.01); C10G 2300/42 (2013.01); C10G 2400/30 (2013.01); Y02P 30/20 (2015.11)
(58) Field of Classification Search
 CPC . C10G 3/47; C10G 3/44; C10G 1/002; C10G 45/30; C10G 2300/1025; C10G 2300/1014; C10G 2300/42; C10G 2400/30; C07C 2/00; C07C 2/54; C07C 2529/40; C07C 2/76; B01J 29/40; B01J 29/42; B01J 29/44; B01J 29/46
 USPC .................................... 585/240, 242, 700
 See application file for complete search history.

(56) References Cited

U.S. PATENT DOCUMENTS

| | | | |
|---|---|---|---|
| 4,933,283 | A | 6/1990 | Chen et al. ............... 435/166 |
| 5,019,663 | A | 5/1991 | Chou et al. ............... 585/415 |
| 6,207,609 | B1 | 3/2001 | Gao et al. ............... 502/177 |
| 7,022,888 | B2* | 4/2006 | Choudhary et al. ........ 585/639 |
| 8,742,189 | B2* | 6/2014 | Kiesslich et al. ........ 585/417 |
| 2010/0185033 | A1* | 7/2010 | Karim et al. ............ 585/408 |
| 2011/0047864 | A1* | 3/2011 | Bhan et al. ............. 44/307 |
| 2011/0124933 | A1* | 5/2011 | Kiesslich .............. B01J 29/48 585/417 |

OTHER PUBLICATIONS

Gullu et al., Biomass to methanol via pyrolysis process, Energy Conversion and Management 42, Elsevier, 2001, p. 1349-1356.*
Adjaye, J. D. et al. (1994) Upgrading of a wood-derived oil over various catalysts, *Biomass Bioenergy* 7(1-6), 201-211.
Adjaye, J. D. et al. (1995) Production of hydrocarbons by catalytic upgrading of a fast pyrolysis bio-oil. Part II: Comparative catalyst performance and reaction pathways, *Fuel Processing Technology* 45, 185-202.
Adjaye, J. D. et al. (1995) Production of hydrocarbons by catalytic upgrading of a fast pyrolysis bio-oil. Part I: Conversion over various catalysts, *Fuel Processing Technology* 45, 161-183.
Bridgwater, A. V. (1996) Production of high grade fuels and chemicals from catalytic pyrolysis of biomass, *Catal. Today* 29(1-4), 285-295.
Carlson, T. R. et al. (2009) Mechanistic Insights from Isotopic Studies of Glucose Conversion to Aromatics Over ZSM-5, *ChemCatChem* 1(1), 107-110.
Carlson, T. R. et al. (2010) Catalytic fast pyrolysis of glucose with HZSM-5: The combined homogeneous and heterogeneous reactions, *Journal of Catalysis* 270, 110-124.
Chheda, J. N. et al. (2007) Liquid-Phase Catalytic Processing of Biomass-Derived Oxygenated Hydrocarbons to Fuels and Chemicals, *Angewandte Chemie Int. Ed.* 46, 7164-7183.
Corma, A. et al. (2007) Processing biomass-derived oxygenates in the oil refinery: Catalytic cracking (FCC) reaction pathways and role of catalyst, *J. Catal.* 247(2), 307-327.
Donnis, B. et al. (2009) Hydroprocessing of Bio-Oils and Oxygenates to Hydrocarbons. Understanding the Reaction Routes, *Topics in Catalysis* 52(3), 229-240.

Elliott, D. C. et al. (1991) Developments in direct thermochemical liquefaction of biomass: 1983-1990, *Energy Fuels* 5(3), 399-410.
Gayubo, A. G. et al. (2004) Transformation of Oxygenate Components of Biomass Pyrolysis Oil on a HZSM-5 Zeolite, I. Alcohols and Phenols, *Industrial & Engineering Chemistry Research* 43, 2610-2618.
Höök, M. et al. (2009) A review on coal to liquid fuels and its coal consumption, *International Journal of Energy Research* 34(10), 848-864.
Horne, P. A. et al. (1996) Upgrading of biomass-derived pyrolytic vapours over zeolite ZSM-5 catalyst: effect of catalyst dilution on product yields, *Fuel* 75(9), 1043-1050.
Huber, G. W. et al. (2006) Synthesis of transportation fuels from biomass: chemistry, catalysis, and engineering, *Chem. Rev.* 106, 4044-4098.
Iliuta, M. C. et al. (2002) Methane Nonoxidative Aromatization over Ru—Mo/HZSM-5 in a Membrane Catalytic Reactor, *Ind. Eng. Chem. Res.* 41(10), 2371-2378.
Ismagilov, Z. R. et al. (2008) Direct conversion of methane on Mo/ZSM-5 catalyst to produce benzene and hydrogen: achievements and perspective, *Energy and Environment Science* 1, 526-541.
Li, W.-Y. et al. (1998) Ni/ZSM-5 Catalyst for $CH_4$ Reforming with $CO_2$, *Pet. Sci. Technol.* 16(5), 539-553.
Lubango, L. M. et al. (2002) Light alkanes aromatization to BTX over Zn—ZSM-5 catalysts—Enhancements in BTX selectivity by means of a second transition metal ion, *Applied Catalysis A: General* 235, 265-272.
Mohan, D. et al. (2006) Pyrolysis of wood/biomass for bio-oil: A critical review, *Energy Fuels* 20(3), 848-889.
Noyori, R. et al. (2001) Metal-Ligand Bifunctional Catalysis: A Nonclassical Mechanism for Asymmetric Hydrogen Transfer between Alcohols and Carbonyl Compounds, *J. Org. Chem.* 66(24), 7931-7944.
Paine, J. B. et al. (2008) Carbohydrate pyrolysis mechanisms from isotopic labeling Part 2. The pyrolysis of D-glucose: General disconnective analysis and the formation of C1 and C2 carbonyl compounds by electrocyclic fragmentation mechanisms, *J. Anal. Appl. Pyrolysis* 82, 10-41.
Paine, J. B. et al. (2007) Carbohydrate pyrolysis mechanisms from isotopic labeling: Part 1: The pyrolysis of glycerin: Discovery of competing fragmentation mechanisms affording acetaldehyde and formaldehyde and the implications for carbohydrate pyrolysis, *J. Anal. Appl. Pyrolysis* 80(2), 297-311.
Patwardhan, P. R. et al. (2009) Product distribution from fast pyrolysis of glucose-based carbohydrates, *J. Anal. Appl. Pyrolysis* 86, 323-330.
Petrus, L. et al. (2007) Biomass to Biofuels, a Chemical Perspective, *Green Chem.* 8, 861-867.
Shirazi, L. et al. (2008) The effect of Si/Al ratio of ZSM-5 zeolite on its morphology, acidity and crystal size, *Cryst. Res. Technol.* 43(12), 1300-1306.
Sily, P. D. et al. (2006) Methane direct conversion on Mo/ZSM-5 catalysts modified by Pd and Ru, *Journal of Natural Gas Chemistry* 15, 82-86.
van Santen, R. A. (1991) Chemical basis of metal catalyst promotion, *Surf. Sci.* 251-252, 6-11.
Wang, L. et al. (1995) Activation and aromatization of methane and ethane over Mo(VI)/HZSM-5 and W(VI)/HZSM-5 zeolites catalysts, in *Studies in Surface Science and Catalysis* (H.K. Beyer, H. G. K. I. K., et al., Eds.), pp. 495-500, Elsevier.
Zheng, L. et al. (2006) Non-Oxidative Aromatization of $CH_4$—$C_3H_8$ over La-Promoted Zn/HZSM-5 Catalysts, *J. Nat. Gas Chem.* 15(1), 52-57.

* cited by examiner

Metal impregnated ZSM-5

Methane Steam Reforming: $CH_4 + H_2O \rightarrow H_2 + CO_2$

Biomass Oxygenates Dehydrative Aromatization: $C_xH_yO_z + H_2 \rightarrow BTEX + H_2O$

Overall: $C_xH_yO_z + CH_4 \rightarrow BTEX + CO_2$

DEOXYGENATION OF BIOMASS DERIVED OXYGENATES TO HYDROCARBONS VIA DIRECT METHANE INTERVENTION

FIELD OF THE INVENTION

The present invention relates to a method for the production of organic chemicals, predominantly the production of aromatic molecules such as benzene, toluene, ethyl benzene, and xylenes, through the use of coupling short-chain hydrocarbons to deoxygenate biomass derived oxygenates.

BACKGROUND OF THE INVENTION

Methods for conversion of solid biomass into liquids by acid hydrolysis, pyrolysis, and liquefaction are well known (Klass 1998) [1]. A wide range of products are produced from the above reactions including: cellulose, hemicellulose, lignin, polysaccharides, monosaccharides (e.g. glucose, xylose, galactose), furfural, polysaccharides, and lignin derived alcohols (coumaryl, coniferyl and sinapyl alcohols). Bio-oils, which are a mixture of over 300 different compounds, can also be produced by liquefaction or fast pyrolysis (Elliott, Beckman et al. 1991) [2]. What is needed is a process for the efficient conversion of biomass to hydrocarbons using available resources.

SUMMARY OF THE INVENTION

The present invention relates to a process where methane or any short chained hydrocarbon is catalytically coupled with an oxygenate (preferably derived from thermal processing of biomass) to dehydrate and produce a deoxygenated hydrocarbon. The presence of oxygen in biomass derivatives adversely affects its ability to be further processed into hydrocarbon fuels because the resulting water poisons many catalysts (including alumina containing catalysts, zeolites, etc.) found in petrochemical refineries. While commonly used hydrodeoxygenation methods require expensive hydrogen to instigate deoxygenation, the present process uses short chained hydrocarbons (such as methane or natural gas) to instigate hydrodeoxygenation.

Methods for conversion of solid biomass into liquids by acid hydrolysis, pyrolysis, and liquefaction are well known (Klass 1998) [1]. A wide range of products are produced from the above reactions including: cellulose, hemicellulose, lignin, polysaccharides, monosaccharides (e.g. glucose, xylose, galactose), furfural, polysaccharides, and lignin derived alcohols (coumaryl, coniferyl and sinapyl alcohols). Bio-oils, which are a mixture of over 300 different compounds, can also be produced by liquefaction or fast pyrolysis (Elliott, Beckman et al. 1991) [2].

Fluid catalytic cracking (FCC) is the most widely used process for the conversion of crude oil into gasoline and other hydrocarbons. The FCC process consists of two reactor vessels coupled together. In the first reactor a hot particulate catalyst is contacted with hydrocarbon feedstocks in a riser reactor to crack the feedstock, thereby producing cracked products and spent coked catalyst. After the cracking reaction takes place the catalyst is largely deactivated by coke. The coked catalyst is separated from the cracked products, stripped of residual oil by a series of baffles in a downflow reactor by steam stripping, and then regenerated by burning the coke from the coked catalyst in a regenerator. The regeneration process occurs at 650-760° C. and a pressure around 3 atmospheres (atm) to burn off coke. The hot catalyst is then recycled to the riser reactor for additional cracking.

A variety of process configurations and catalysts have been developed for the FCC process. FCC catalysts usually contain mixtures of a Y-zeolite within a silica-alumina matrix although other compositions are also known to those skilled in the art. Using FCC processes for biomass conversion does not require a significant capital investment as FCC plants are already installed in petroleum refineries. It would therefore represent a considerable advance in the state of the art if efficient methods were developed to use the FCC process to convert biomass-derived molecules into fuels and chemicals.

In one embodiment the invention is a method for the production of aromatic hydrocarbons from biomass-derived molecules. Several methods have been reported for conversion of biomass-derived molecules into liquid fuels using zeolite catalysts. Chen and Koenig in U.S. Pat. No. 4,933,283 [3] and U.S. Pat. No. 4,549,031 (Mobil) [4] report a process for conversion of biomass derived carbohydrates, starches and furfural into liquid hydrocarbon products, CO and coke by passing aqueous streams over zeolite catalysts at 500° C. [3, 4]. They observed that 40-66% of the carbon converts to coke when xylose, glucose, starch and sucrose are fed over a ZSM-5 catalyst at 500° C. [4]. Other products formed included hydrocarbons, CO and $CO_2$. They also report that mixing the aqueous-carbohydrate streams with methanol leads to lower levels of coke and higher levels of hydrocarbons. Chou and Melconian in U.S. Pat. No. 5,019,663 discloses a method of processing low value light paraffin into more valuable olefinic and aromatic compounds using a zeolite catalyst [5]. U.S. Pat. No. 5,019,663 focuses upon the process of aromatizing $C_2$-$C_4$ parafinnic compound streams (liquid petroleum gas, LPG) in combination with an oxygenate stream (such as methanol) [5]. U.S. Pat. No. 5,019,663 even discusses optimizing the process for $C_6$-$C_8$ BTX hydrocarbons. U.S. Pat. No. 5,019,663 does not disclose the use of biomass or biomass-derived products, nor does it discuss using methane steam reforming [5].

In one embodiment the invention is a method for the production of BTEX from biomass derived oxygenates using a zeolite based catalyst in combination with methane steam reforming. Catalytic conversion of light alkanes, predominantly propane, into aromatic BTEX products over a ZSM-5 catalyst has been reported by Lubango et al. in 2002 [6]. The focus of this article is the improvement in yield and selectivity by variation of the second transition metal ion in the catalyst [6]. Lubango does not disclose the use of biomass or methane steam reforming.

Horne et al. 1996 discloses processing of biomass in the form of waste wood chips in a fluidized bed reactor at 550° C. to maximize formation of pyrolytic vapours that were subsequently passed over a ZSM-5 zeolite catalyst [7]. While significant quantities of aromatic hydrocarbons were not produced, aromatic hydrocarbons that were detected are directly attributed to the presence of the ZSM-5 zeolite catalyst, particularly when the catalyst included steel [7]. Horne et al. does not disclose introduction of methane, methanol, or other small chain hydrocarbon for the processing of the biomass [7]. Petrus et al. 2006 discusses the removal of oxygen from carbohydrate-rich biomass and upgrading the materials to higher alkanes [8]. Petrus discusses using the Fischer-Tropsch reaction to generate alkane chains from carbon monoxide and hydrogen. Petrus et al. further discusses eliminating oxygen from carbohydrates in biomass as an automatic conversion route with synthesis gas as an intermediate from which higher alkanes (i.e for diesel) can be derived by the Fischer-Tropsch reaction [8]. This reference does not disclose a process to produce BTX from biomass nor does it specifically describe catalysts used in such a process [8].

Corma et al. 2007 discloses FCC processing of glycerol and sorbitol as representative biomass-derived oxygenates [9]. A catalyst used in this study was a ZSM-5-based FCC additive. In this process, oxygen is removed from the glycerol and sorbitol as water, carbon monoxide, or carbon dioxide. The oxygen is removed through the following reaction: $C_6O_6H_{12} \rightarrow aC_xH_{2x}+2O_y+bCO_2+cH_2O+dCO+eC$. Corma et al. discusses several internal reactions (both hydrogen generating and hydrogen consuming) occurring during the FCC processing including the WGS, steam reforming, dehydrogenation, and decarbonylation. Corma et al. does not discuss linking other feedstocks (such as methane, natural gas, or syn-gas) to the processing of biomass derived oxygenates.

Bio-oils, produced by fast pyrolysis or liquefaction from biomass, are a mixture of more than 300 compounds. Bio-oils are thermally unstable and need to be upgraded if they are to be used as fuels. Bio-oils, and bio-oil components, can be converted into more stable fuels using zeolite catalysts (Bridgwater 1996) [10]. Reaction conditions used for the above process are temperatures from 350-500° C., atmospheric pressure and gas hourly space velocities of around 2. The products from this reaction include hydrocarbons (aromatic, aliphatic), water soluble organics, water, oil soluble organics, gases ($CO_2$, CO, light alkanes), and coke. During this process a number of reactions occur, including dehydration, cracking, polymerization, deoxygenation, and aromatization. However poor hydrocarbon yields and high yields of coke generally occur under reaction conditions, limiting the usefulness of zeolite upgrading.

In one embodiment, the present invention contemplates a method where methane or any short chained hydrocarbon is reacted in the presence of a catalyst with an oxygenate (preferably derived from thermal processing of biomass) to dehydrate and produce a deoxygenated hydrocarbon. The presence of oxygen in biomass derivatives adversely affects its ability to be further processed into hydrocarbon fuels because the resulting water poisons many catalysts (including alumina containing catalysts, zeolites, etc.) found in petrochemical refineries. In another embodiment the invention further comprises a method which uses short chained hydrocarbons (such as methane or natural gas) to instigate hydrodeoxygenation a biomass derived oxygenate. In another embodiment the invention further comprises said method, wherein said biomass derived oxygenate is glucose. In another embodiment the invention further comprises said method, wherein said biomass derived oxygenate is methanol.

In one embodiment, the present invention contemplates a method, comprising, a) providing, i) a short chained hydrocarbon; ii) a catalyst; and ii) a biomass comprising an oxygenate and b) reacting said hydrocarbon with said oxygenate in the presence of said catalyst so as to create a reaction coupling hydrocarbon steam reforming and dehydrative aromatization, wherein said oxygenate is dehydrated and a deoxygenated hydrocarbon is produced. In one embodiment, said hydrocarbon steam reforming and dehydrative aromatization reactions are concurrent. In one embodiment, said hydrocarbon steam reforming and dehydrative aromatization reactions are interdependent. In one embodiment, said short chained hydrocarbon is methane. In one embodiment, said short chained hydrocarbon is derived from natural gas. In one embodiment, said oxygenate is derived from thermal processing of biomass. In one embodiment, said oxygenate is glucose. In one embodiment, said oxygenate is methanol. In one embodiment, said deoxygenated hydrocarbon is an aromatic hydrocarbon. In one embodiment, said aromatic hydrocarbon is selected from the group consisting of benzene, benzene derivatives, toluene, and xylenes. In one embodiment, said catalyst is a zeolite catalyst. In one embodiment, said zeolite catalyst is HZSM-5. In one embodiment, said zeolite catalyst is ZSM-5. In one embodiment, said zeolite catalyst is a carborized molybdenum catalyst. In one embodiment, said zeolite catalyst is platinized ZSM-5. In one embodiment, said reacting is performed without the direct intervention of hydrogen. In one embodiment, said reaction generates molecular hydrogen. In one embodiment, said hydrogen reacts with said oxygenates so as to aromatize said oxygenates, thereby removing oxygen in the form of water. In one embodiment, the invention comprises the deoxygenated hydrocarbons produced according to the aforementioned method.

In another embodiment the invention contemplates a method, comprising, a) providing, i) a short chained hydrocarbon; ii) a catalyst; and iii) a biomass comprising one or more oxygenates; and b) reacting said hydrocarbon with said oxygenate in the presence of said catalyst so as to cause two aromatization reactions, wherein said one or more oxygenates are dehydrated and one or more deoxygenated hydrocarbons are produced. In one embodiment, said aromatization reactions are concurrent. In one embodiment, said aromatization reactions are interdependent. In one embodiment, said reacting of step b) is carried out at a temperature between approximately 300-800° C. In one embodiment, said reacting is carried out at atmospheric pressure. In one embodiment, said reacting is carried out at elevated pressure. In one embodiment, said elevated pressure is between approximately 20-100 psi. In one embodiment, said short chained hydrocarbon is methane and said reacting causes methane to form aromatic compounds. In one embodiment, said reacting is performed without the direct intervention of hydrogen. In one embodiment, said reaction generates molecular hydrogen. In one embodiment, said hydrogen reacts with said oxygenates so as to aromatize said oxygenates, thereby removing oxygen in the form of water. In one embodiment, the invention comprises the deoxygenated hydrocarbons produced according to the aforementioned method.

In another embodiment the invention contemplates, a method, comprising, a) providing, i) a short chained hydrocarbon; ii) a catalyst; and iii) a biomass comprising one or more oxygenates; and b) reacting said hydrocarbon with said oxygenate in the presence of said catalyst thereby creating a hydrogen generating reaction that is kinetically coupled with a hydrogen consuming reaction on a single catalyst surface. In one embodiment, said hydrogen generating reaction and hydrogen consuming reaction are concurrent. In one embodiment, said hydrogen generating reaction and hydrogen consuming reaction are interdependent.

BRIEF DESCRIPTION OF THE DRAWINGS

For a more complete understanding of the features and advantages of the present invention, reference is now made to the detailed description of the invention along with the accompanying figures.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Short-chain hydrocarbons include: methane, ethane, propane, butane, any alkane with the general formula $C_xH_{2x+2}$ where x is 4 or less, any alkene with the general formula $C_xH_{2x}$ where x is 4 or less, or any alkyne with the general formula $C_xH_{2x-2}$ where x is 4 or less.

Natural gas is a combustible gas typically from underground petroleum deposits used for cooking and heating. Components of natural gas include short-chain hydrocarbons (methane, ethane, propane, butane), $CO_2$, $N_2$, and $H_2S$.

Biomass-derived oxygenates include: cellulose, hemicellulose, lignin, polysaccharides, monosaccharides (e.g. glucose, xylose, galactose), furfural, polysaccharides, lignin derived alcohols (coumaryl, coniferyl and sinapyl alcohols), and molecules derived from the above listed molecules. Mixtures of these compounds, such as those found in bio-oils derived from pyrolysis or liquefaction, are also included in the biomass-derived oxygenates definition.

Zeolite catalyst is a hydrated aluminum and calcium (or sodium) silicate (for example, $CaO.2Al_2O_3.5SiO_2$ or $Na_2O.2Al_2O_3.5SiO_2$) made with controlled porosity, used as a catalytic cracking catalyst in petroleum refineries, or loaded with catalyst for other chemical reactions. One example of a zeolite catalyst is ZSM-5. ZSM-5, Zeolite Sieve of Molecular porosity (or Zeolite Socony Mobil)-5, (structure type MFI-Mordenite Framework Inverted) is an aluminosilicate zeolite mineral belonging to the pentasil family of zeolites. Its chemical formula is $Na_nAl_nSi_{96-n}O_{192}.16H_2O$ (0<n<27). Patented by Mobil Oil Company in 1975, it is widely used in the petroleum industry as a heterogeneous catalyst for hydrocarbon isomerization reactions [11]. For HZSM-5, the zeolite ion exchange sites are occupied by H+ ions. This is normally done by ion exchanging the zeolite with $NH_4Cl$ to produce a $NH_4$+ exchanged zeolite. That zeolite is then heated to decompose the $NH_4$+ to H+ and ammonia. ZSM-5 is more general in that any ions can occupy the ion exchange sites. Catalysts are often termed promoted or unpromoted. A promoted catalyst, such as promoted ZSM-5, are treated to improve a particular catalytic function. The role of promotors or modifiers is to enhance selectivity by changing the active catalyst surface such that the number of reaction paths offered to adsorbed molecules decreases and a selected reaction path dominates. A promotor is an additive added to the catalyst when the catalyst is prepared; a modifier alters selectivity and activity by introduction of the coadsorbent during reaction from the gas or Liquid phase [12]. Such promoted catalysts can be prepared for example by a metal impregnation method. An added metal may include transition metals or alkali metals. Hydrogen may also be added in the impregnation method. Examples of such metal impregnated ZSM-5 catalysts are platinized ZSM-5, Cu/ZSM-5, Fe/ZSM-5, and Ni/ZSM-5 (used as a catalyst for $CH_4$ reforming with $CO_2$ [13].

Bifunctional catalyst is a catalytic substance that possesses two catalytic sites and thus is capable of catalyzing two different types of reactions. Bifunctional catalysts are also known as dual-function catalyst. A bifunctional catalyst is term coined to refer to a specific set of hydrogenation catalyst containing Lewis acid and Lewis base [14].

Lewis acid, A, is a chemical substance that can accept a pair of electrons from a Lewis base, B, that acts as an electron-pair donor, forming an adduct, AB as given by the following:

$$A+:B \rightarrow A-B$$

Gilbert N. Lewis proposed this definition, which is based on chemical bonding theory, in 1923.

A Lewis base is an atomic or molecular species that has a lone pair of electrons in the HOMO. Typical examples are: compounds of N, P, As, Sb and Bi in oxidation state 3; compounds of O, S, Se and Te in oxidation state 2, including water, ethers, ketones, sulphoxides; and molecules like carbon monoxide. An easy way to remember this concept is that nearly all of the compounds formed by the transition elements are coordination compounds, wherein the metal or metal ion is a Lewis acid and the ligands are Lewis bases.

A carborized molybdenum catalyst is a catalyst produced when a molybdenum carbide compound is formed by reacting a molybdate with a mixture of hydrogen and carbon monoxide. By heating the molybdate powder from a temperature below 300° C. to maximum temperature 850° C., a controlled reaction can be conducted wherein molybdenum carbide is formed. A high surface area, nanograin, metastable molybdenum carbide can be formed when the reaction temperature is below 750° C. The metastable molybdenum carbide is particularly suitable for use as a catalyst for the methane dry reforming reaction [15].

Dehydration catalyst is a catalyst which aids in the removal of water ($H_2O$) molecules in a reaction. An example of a dehydration catalyst would be a ZSM-5 where the ratio of Si:Al=40. The ratio of silicon to aluminum has a significant effect on the catalytic effects of the zeolite [16]. ZSM-5 synthesized with different Si/Al molar ratios had different morphologies and particle sizes. It was found that the average ZSM-5 crystal size increased as Si/Al molar ratio increased [16].

BTEX is an acronym that stands for benzene, toluene, ethylbenzene, and xylenes. These compounds are some of the volatile organic compounds (VOCs) found in petroleum derivatives such as petrol (gasoline).

"Hydrodeoxygenation" (HDO) is a hydrogenolysis process removing oxygenated compounds from the fast pyrolysis derived bio-oil using commercial hydrotreating catalysts in the form of water. Hydrotreating catalyst commonly uses are nickel-molybdenum or cobalt-molybdenum on gamma alumina, zeolites (ZSM-5), palladium on carbon and platinum on carbon as well as alumina.

"Fischer-Tropsch" (FT) synthesis is a catalyzed chemical reaction in which synthesis gas, a mixture of carbon monoxide and hydrogen, is converted into liquid hydrocarbons of various forms. The most common catalysts are based on iron and cobalt, although nickel and ruthenium have also been used. The principal purpose of this process is to produce a synthetic petroleum substitute, typically from coal, natural gas or biomass, for use as synthetic lubrication oil or fuel.

FT synthesis equation: $(2n+1)H_2 + nCO \rightarrow C_nH_{(2n+2)} + nH_2O$

"Water-gas shift reaction" (WGS/Dussan Reaction) is a chemical reaction in which carbon monoxide reacts with water to form carbon dioxide and hydrogen.

Water gas shift reaction equation: $H_2O + CO \rightarrow H_2 + CO_2$

"Steam methane reforming" (SMR) or methane steam reforming is the most common method of producing commercial bulk hydrogen; it is also seen in combination with a lower temperature gas-shift reaction.

Steam methane reforming (SMR) equation: $CH_4 + H_2O \rightarrow CO + 3H_2$

Gas-shift reaction equation: $CO + H_2O \rightarrow CO_2 + H_2$

"Biomass gasification" (BG) is a process that converts carbonaceous materials, such as coal, petroleum, biofuel, or biomass, into carbon monoxide and hydrogen by reacting the raw material, such as house waste, or compost at high temperatures with a controlled amount of oxygen and/or steam. The resulting gas mixture is called synthesis gas (or syn-gas) which is itself a fuel. Syn-gas may be burned directly in internal combustion engines, used to produce methanol and hydrogen, or converted via the Fischer-Tropsch process into synthetic fuel. Gasification can also begin with materials that are not otherwise useful fuels, such as biomass or organic waste. In addition, the high-temperature combustion refines out corrosive ash elements such as chloride and potassium, allowing clean gas production from otherwise problematic fuels.

"Fluid catalytic cracking" (FCC) is the most important conversion process used in petroleum refineries. It is widely used to convert the high-boiling, high-molecular weight hydrocarbon fractions of petroleum crude oils to more valuable gasoline, olefinic gases and other products.

"Dehydrative aromatization" is a reaction which results in the aromatization of a compound as a result of the loss of at least one $H_2O$ molecule.

The CDS Pyroprobe® Model 5200 is a thermal sample preparation instrument produced by CDS Analytical, Inc. Platinum filaments are rapidly heated for pulse pyrolysis work, or slowly heated with controlled rates for programmed analyses. Temperatures may be set in 1° C. increments up to 1400° C. for a wide heating range and more precise pyrolysis temperatures. Analytical runs may be programmed for up to eight steps per sample, with automatic control of the on-line valve, interface temperature, GC ready sensing and GC start for each step. When configured with the trapping option, the Pyroprobe® may be used to collect analytes from slow rate pyrolysis, thermal desorption or reactant gas pyrolysis. The unique interfacing design permits a direct pyrolysis path to the GC inlet or rapid sample heating and transfer to the trap without interrupting the pneumatics of the GC. Simple PC control of all parameters is presented in a program window, permitting method development, storage, notation, and editing.

Aromatization—A reaction that forms an arene compound from an unsaturated or partially unsaturated cyclic precursor is simple called an aromatization (reaction). An aromatic hydrocarbon (abbreviated as AH) or arene (or sometimes aryl hydrocarbon) is a hydrocarbon with a conjugated cyclic molecular structure that is much more stable than the hypothetical localized structure. The term 'aromatic' was assigned before the physical mechanism determining aromaticity was discovered, and was derived from the fact that many of the compounds have a sweet scent. The configuration of six carbon atoms in aromatic compounds is known as a benzene ring, after the simplest possible such hydrocarbon, benzene. Aromatic hydrocarbons can be monocyclic or polycyclic. Some non-benzene-based compounds called heteroarenes, which follow Mückel's rule, are also aromatic compounds. In these compounds, at least one carbon atom is replaced by one of the heteroatoms oxygen, nitrogen, or sulfur. Examples of non-benzene compounds with aromatic properties are furan, a heterocyclic compound with a five-membered ring that includes an oxygen atom, and pyridine, a heterocyclic compound with a six-membered ring containing one nitrogen atom.

Coupling—in terms of chemical reaction coupling refers to when two reactions are combined where a product of one reaction serves as a reactant for a subsequent reaction. The overall reaction reflects the coupling of the combined reactions.

Interdependent—in terms of chemical reactions refers to reactions depending on each other which are unable to proceed without each other. Such reactions with mutually dependent reactants and/or products.

Concurrent—in terms of chemical reactions refers to reactions operating or occurring at the same time, running parallel, or acting in conjunction.

Pyrolysis is the process of thermal decomposition to produce gases, liquids (tar), and char (solid residue). These pyrolysis products can all be used as fuels, with or without prior upgrading, or they can be utilized as feedstocks for chemical or material industries. The types of materials which are candidates for pyrolysis processing include coal, plant biomass, animal and human waste, food scraps, paper, cardboard, plastics, and rubber.

DETAILED DESCRIPTION OF THE INVENTION

Studies on concurrent co-processing of methane with glucose with the target of producing liquid hydrocarbon fuels have demonstrated that it is possible to remove oxygen from oxygenates without direct intervention of hydrogen gas. Using a platinized ZSM-5 bifunctional catalyst, it was demonstrated that methane could be directly coupled with oxygen in oxygenates producing water and carbon dioxide. The constituents of the remainder of the product stream were effusive amounts of gasoline range hydrocarbons.

The current biomass-to-hydrocarbon technologies (for example, pyrolysis of biomass followed by upgrading of resultant bio-oil) involve hydrodeoxygenation of biomass-derived oxygenates, which consumes tremendous amounts of hydrogen and therefore impact the economy and sustainability of biomass-derived liquid hydrocarbon fuels. Present experiments indicate that it is possible to replace hydrogen with hydrogen-rich, less expensive, and readily available methane to directly deoxygenate bio-based liquids for synthetic fuels production.

Unpromoted HZSM-5 cannot activate methane. However, unpromoted or promoted HZ SM-5 can activate and aromatize oxygenates to a hydrocarbon stream that primarily consists of benzene, toluene, ethyl benzene and xylenes (BTEX) [17]. Similarly, HZSM-5 promoted with metals can aromatize methane [18-22]. A direct result of methane aromatization is the generation of surplus hydrogen that stays adsorbed in the catalyst matrix and would end up as molecular $H_2$ if not utilized. The initial idea was to harness this surplus H for deoxygenating oxygenates via dehydration since excessive coking instantaneously shuts down the catalyst if oxygenate deoxygenation is carried out with limited $H_2$. Therefore, a hydrogen generating reaction was kinetically coupled with a hydrogen consuming reaction on a single catalyst surface.

Example 1

The first set of experiments consisted of pyrolyzing: 1) methane; 2) glucose and 3) a mixture of glucose and methane (all consisting of equivalent carbon composition) over platinized ZSM-5. The experiments were carried out in a CDS 5200 pyroprobe that had an inline GCMS for product analysis.

Figure 1:
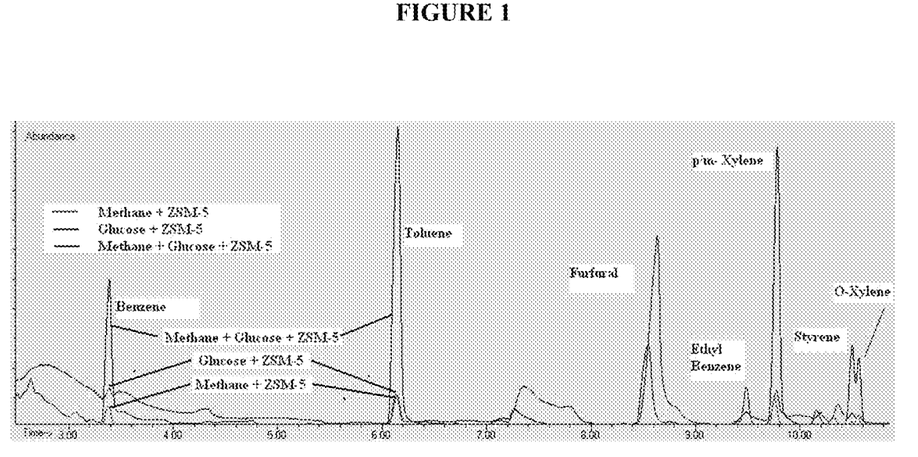
FIG. 1 is a graph showing product composition as analyzed by gas chromatography-mass spectrometry (GCMS) when glucose, methane and a combination of both (equivalent carbon compositions) were aromatized in the presence of ZSM-5 (Si/Al=40). Notice the remarkable increase in HC yields when glucose is aromatized in the presence of methane.

Remarkable changes to product composition where observed when glucose was aromatized in the presence of methane. As seen in FIG. 1, introduction of methane remarkably increased the hydrocarbon yields when glucose was aromatized in the presence of methane as compared to when they were aromatized individually. The furfural (an oxygenated product) yield was also reduced when glucose was aromatized in the presence of methane.

Figure 2:
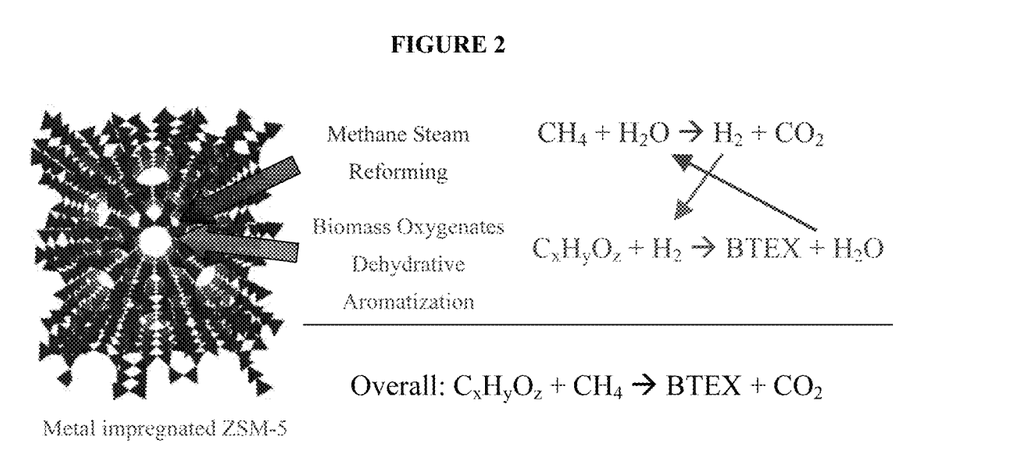
FIG. 2 shows a pictorial depiction of one embodiment of the overall reaction combining methane steam reforming and biomass derived oxygenates undergoing dehydratitive aromatization over a metal impregnated ZSM-5 catalyst to produce BTEX (benzene, toluene, ethylbenzene and xylenes) and carbon dioxide.

These results suggests that one or more of the following reactions can occur at the catalyst surface: In one possible coupling reaction (FIG. 2), the hydrogen gas formed during methane steam reforming serves as an ingredient for oxygenated pyrolytic vapor aromatization. Water formed during oxygenate aromatization will serve as an ingredient for methane steam reforming. In such a scenario, the ultimate products of the reaction are HCs and $CO_2$.

Figure 3:
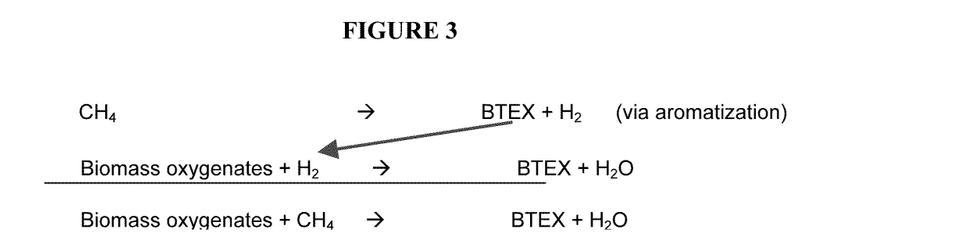
FIG. 3 shows possible concurrently occurring reactions in which hydrogen-rich methane will be aromatized producing BTEX HCs and $H_2$. Oxygenates will utilize this hydrogen and aromatize removing oxygen in the form of water (dehydration).

In another concurrently occurring reaction, hydrogen-rich methane is aromatized to produce BTEX, HCs and $H_2$. Oxygenates will utilize this hydrogen and aromatize removing oxygen in the form of water (dehydration). In one embodiment, this reaction progresses according to the general reaction scheme shown in FIG. 3.

A third possible reaction could occur in the presence of a metal catalyst such that $CH_4$ would activate to CHx and —H moieties. The —H moieties help the dehydration of oxygenates while the CHx moieties directly couple with the oxygen deficient sites of oxygenates propagating to BTEX.

Figure 4:
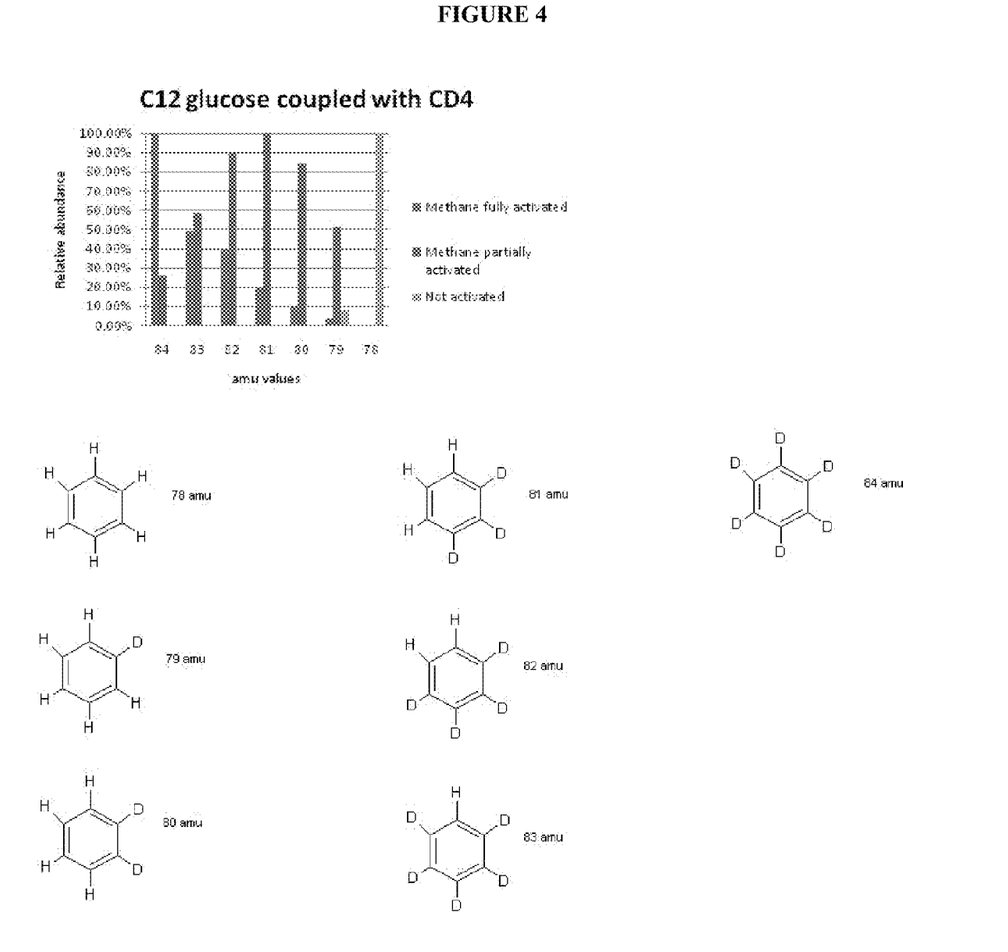
FIG. 4 shows the structures of benzene that were observed during $^{12}C$ glucose aromatization with deuterized methane ($CD_4$).

In order to verify above premises, $^{13}C$ and $^2H$ (D—deuterium) isotope labeled compounds were used during subsequent studies. To determine whether protons from methane actually end up in the deoxygenated products $^{12}C$-labeled glucose and $CD_4$ (duterized-methane) were used. As expected, when $^{12}C$ glucose alone was pyrolysed and passed through the catalyst, 100% of the benzene produced was with a molecular weight of 78 amu. This is depicted as a green bar in the mass-abundance curve generated in the mass spectrum (FIG. 4). When $CD_4$ was used alone the most abundant molecule (blue bars) had a mass of 84 amu, indicating that all hydrogen vacancies are filled with deuterium. However, when $CD_4$ was co-processed with $^{12}C$ glucose, depending on the level of $CD_4$ activation, benzene structures with a range of molecular weights were observed. For example, in the likely event that the catalyst did not fully activate $CD_4$, benzene with partially deuterized ring structure as shown in FIG. 4 with corresponding molecular weights and abundance levels were observed (red bars). This experiment clearly proves that protons from methane actually are transferred to benzene and that methane actually participates in the deoxygenation reaction.

Figure 5:
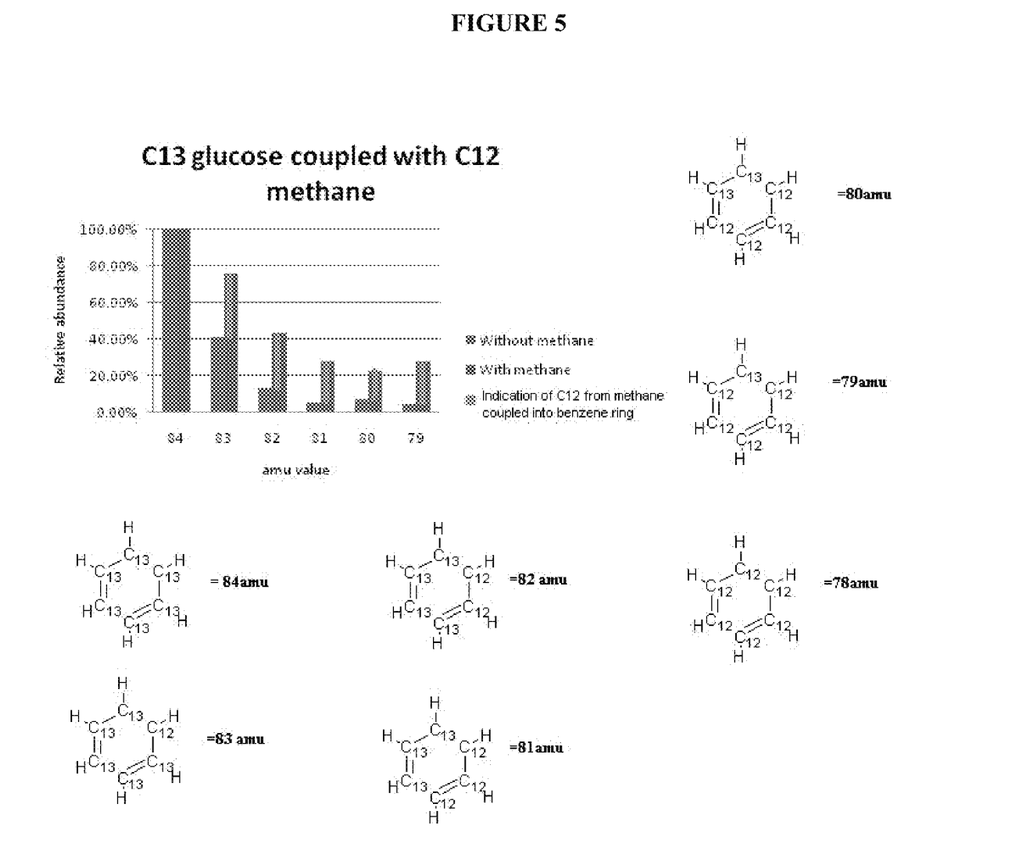
FIG. 5 shows structures of benzene that were observed when $^{13}C$ glucose was co-processed with $^{12}C$ methane ($CH_4$).

The next step focused on finding out where the carbon atoms from methane ended up during glucose deoxygenation. This is crucial since glucose itself has six carbons and it is likely for all the carbon atoms in glucose to end up in the respective benzene structure (although it was determined that hydrogen atoms do transfer from methane into benzene). Also, it is likely that carbon atoms from methane help in oxygen abstraction from glucose by forming $CO_2$ instead of $H_2O$ (which would be partly disadvantageous since formation of $CO_2$ would result in losing valuable carbon that ideally should have ended up in HC product stream). To confirm this, $^{13}C$-labeled glucose and regular $^{12}C$ methane was used during a series of coupling experiments. The benzene produced when pure $^{13}C$-labeled glucose was used had a molecular weight of 84 amu. In case of carbon coupling, $^{12}C$ from methane should transfer to the benzene structure reducing the molecular weight of benzene proportional to the number of carbon atoms transferred from methane. When pure $^{13}C$-labeled glucose was used, the resultant mass spectrum pertinent to benzene consisted of a series of fragments as seen in FIG. 5. However, when $^{13}C$-labeled glucose was co-processed with $^{12}C$ methane, the relative abundance of the fragments having a molecular weight less than 84 amu increased consistently. Since the relative abundance of each fragment for a given molecule is constant irrespective of its concentration, it is quite clear from FIG. 5 that the increase in relative abundance (shown in green) is due to the transfer of $^{12}C$ that was originally in methane to benzene that is predominantly comprised of $^{13}C$ that originally came for glucose. The experiment also confirms that the aromatization reactions that occur are not two independent reactions (i.e., methane aromatization and glucose aromatization) but are two interdependent reactions.

These results are unprecedented in biomass to hydrocarbon biofuels research. The use of hydrogen-rich naturally occurring alkanes as hydrogen carriers and the use of these alkanes over bifunctional shape-selective zeolite catalysts is a departure from existing approaches and have the potential to have a transformative impact on hydrodeoxygenation of biomass for fuels. These results also expose the possibility of co-processing the two most abundant hydrocarbon resources (coal and natural gas) to produce liquid fuels.

Example 2

Figure 6:
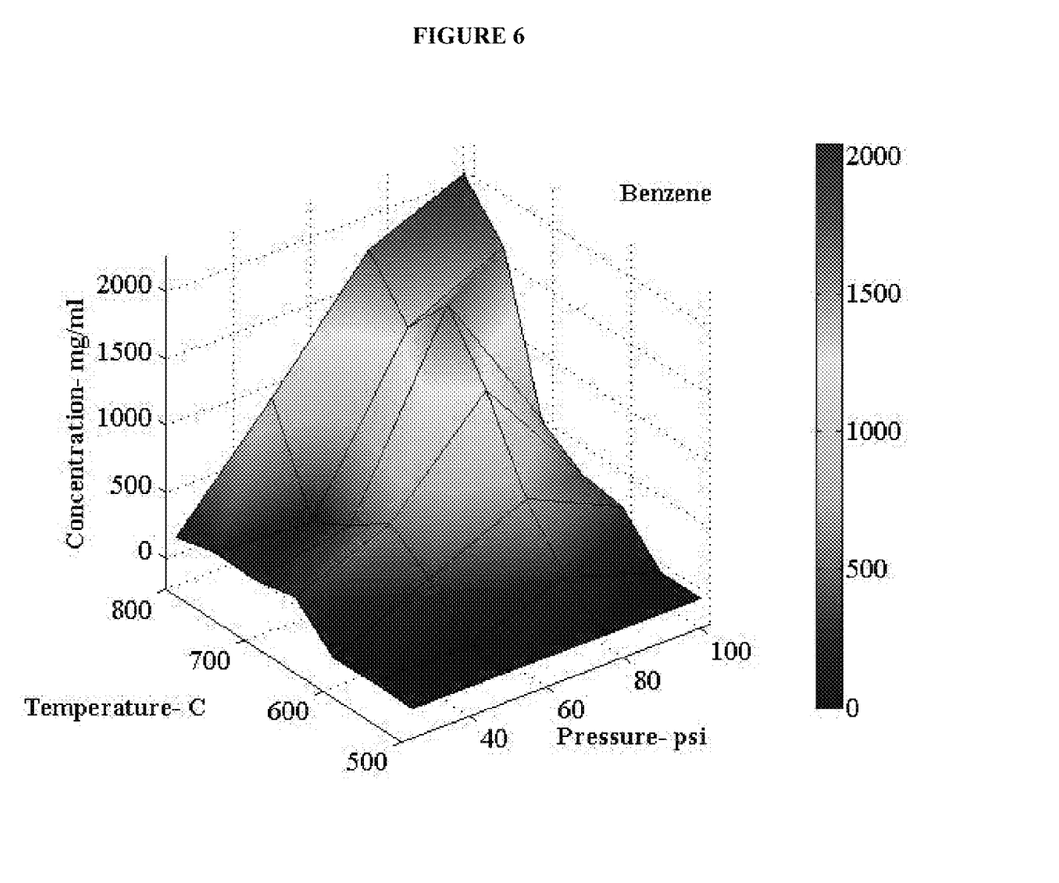
FIG. 6 shows the production of benzene detected by a chromatography-mass spectrometer (GCMS) when the selected model oxygenate methanol was directly pyrolyzed (via a CDS high pressure pyroprobe) to a gas in the presence of a dehydration catalyst (ZSM-5, Si:Al=40).
Figure 7:
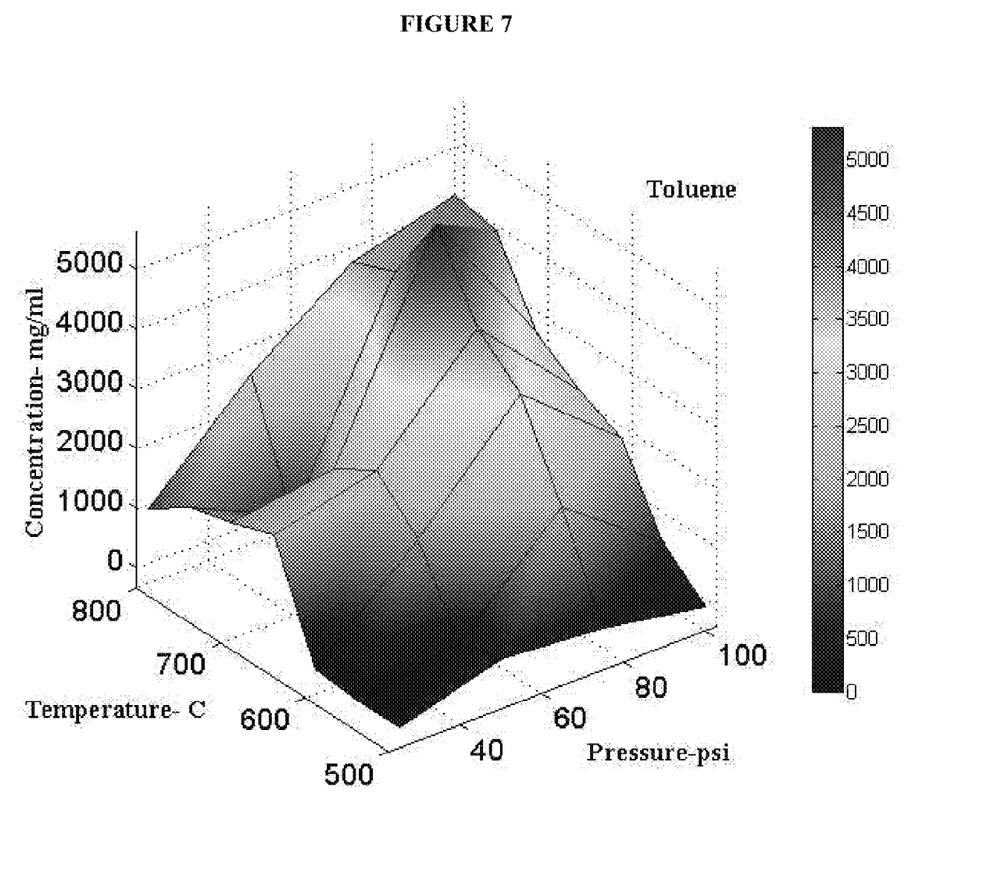
FIG. 7 shows the production of toluene detected by gas chromatography-mass spectrometer (GCMS) when the selected model oxygenate methanol was directly pyrolyzed (via a CDS high pressure pyroprobe) to a gas in the presence of a dehydration catalyst (ZSM-5, Si:Al=40).
Figure 8:
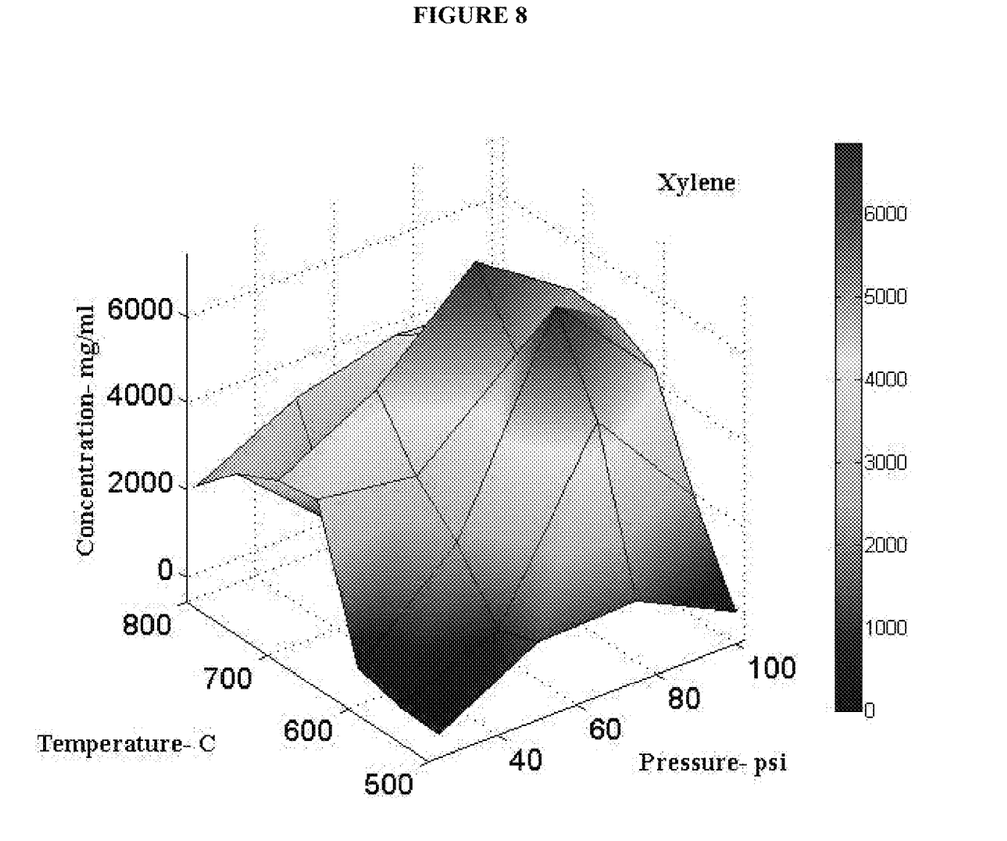
FIG. 8 shows the production of xylenes detected by gas chromatography-mass spectrometer (GCMS) when the selected model oxygenate methanol was directly pyrolyzed (via a CDS high pressure pyroprobe) to a gas in the presence of a dehydration catalyst (ZSM-5, Si:Al=40).

Preliminary studies were conducted to test the hypothesis that methane can be coupled with biomass pyroltic vapor oxygenates to deoxygenate into hydrocarbons over an appropriate catalyst. Preliminary data demonstrates the feasibility of this concept. From the product spectrum that was produced when selected model oxygenate methanol was directly pyrolyzed (via a CDS high pressure pyroprobe) to a GCMS in the presence of a dehydration catalyst (ZSM-5, Si:Al=40), it was evident that effusive amounts of aromatic (gasoline range benzenes, toleuenes and xylenes) and BTEX hydrocarbons (FIG. 6, FIG. 7, and FIG. 8, respectfully) were being produced.

Figure 10:
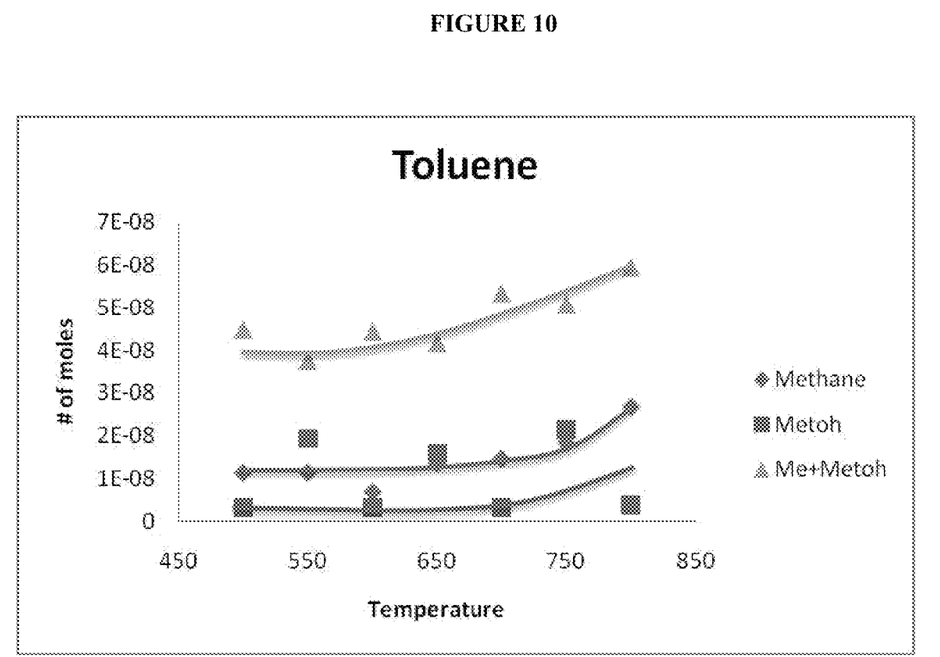
FIG. 10 shows the experimental basis of coupling methane with methanol to produce toluene. Introduction of methane into a methanol aromatization reactor dramatically increased C-7 and C-8 HC yields as opposed to aromatizing either of the reactants alone.
Figure 11:
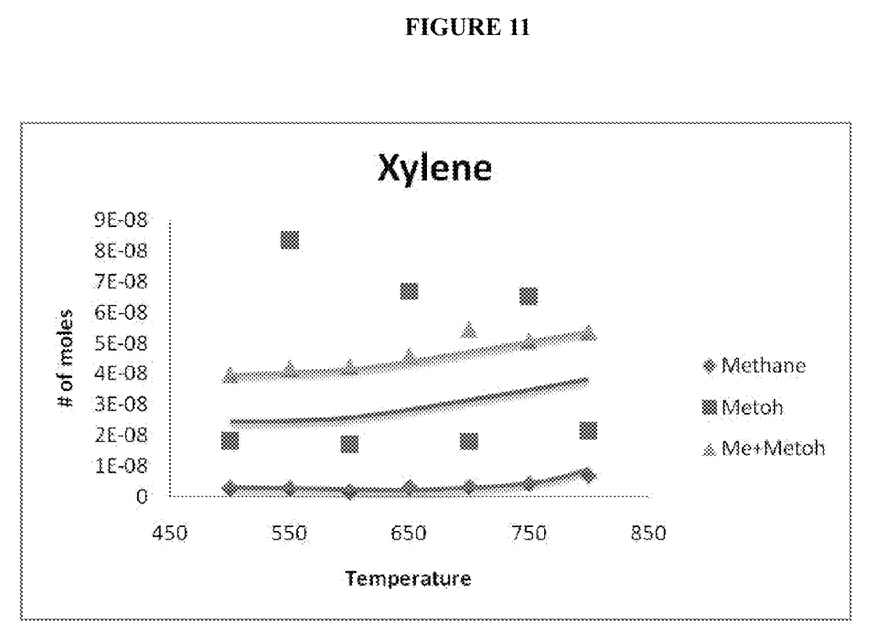
FIG. 11 shows the experimental basis of coupling methane with methanol to produce xylenes. Introduction of methane into a methanol aromatization reactor dramatically increased C-7 and C-8 HC yields as opposed to aromatizing either of the reactants alone.

The results of methanol aromatization with ZSM-5 (Si/Al: 40) under varying pressure is depicted for benzene (FIG. 9), toluene (FIG. 10), and xylenes (FIG. 11). It is evident that at atmospheric pressure, BTEX formation peaks around 700° C. Carrying out the reaction at elevated pressures provides a dramatic increase of aromatic hydrocarbon formation that peaked around 100 PSI. These studies were carried out in a pressurizable pyroprobe reactor that was directly coupled to a GC with duel detectors (Mass Spectrometer (MS) and Flame Ionization Detectors (FID)).

Figure 9:
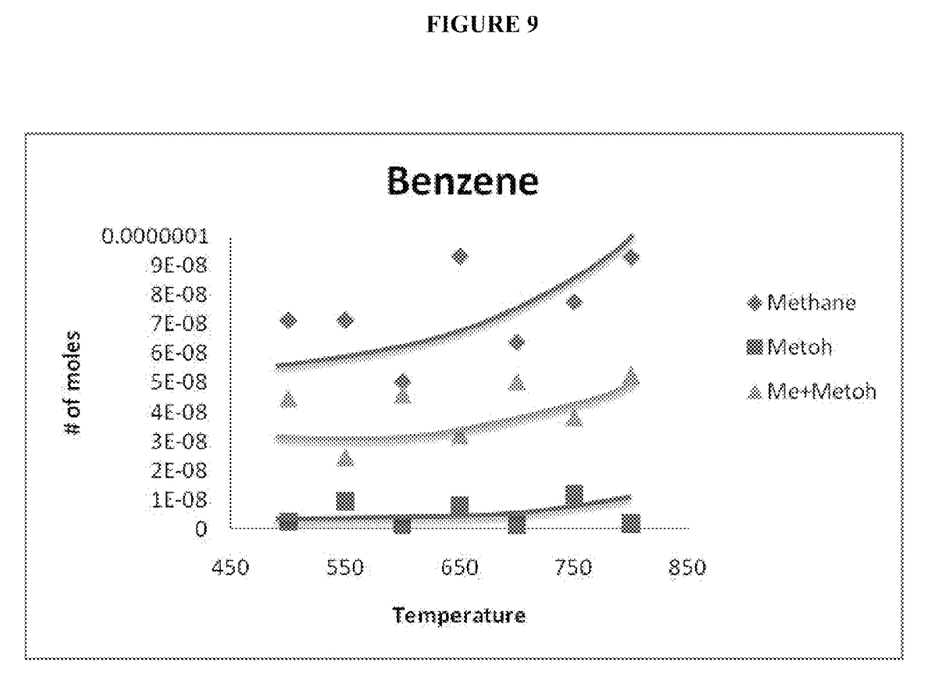
FIG. 9 shows the experimental basis of coupling methane with methanol to produce benzene. Introduction of methane into a methanol aromatization reactor dramatically increased C-7 and C-8 HC yields as opposed to aromatizing either of the reactants alone.

To verify the effect of methane on the aromatization reaction, methane, methanol and mixtures of methane and methanol were pyrolyzed to the GCMS in identical experiments: (i.e. the # of carbon atoms introduced into the reaction chamber at a give time frame was constant, at atmospheric pressure). Results of this study are depicted in FIG. 9 for benzene, FIG. 10 for toluene, and FIG. 11 for xylenes.

It was intriguing to note that introduction of methane (the hydrogen-rich moiety) onto methanol (the oxygen-rich moiety) increased C-7 (toluene) and C-8 (xylenes) yields significantly as compared to introducing any of the reactants alone. This increase was evident throughout the temperatures tested. Although a reduction of benzene yield was observed, (based on literature support) this reduction is believed to be due to the methylation of benzene into a higher HC.

Preliminary data indicates that methane could be used as a direct hydrogen donor for deoxygenating oxygenates instead of using $H_2$ (gas). Based on these observations, three possible reaction pathways are provided:

1) ZSM-5 will dehydroaromatize $CH_3OH$ to BTEX and resultant $H_2O$ will act as an ingredient for the $CH_4$ steam reforming reaction producing $H_2$ and $CO_2$. $H_2$ will assist in the concurrent $CH_3OH$ dehydration reaction.

2) In the acidic sites of ZSM-5, $CH_4$ will aromatize into BTEX and the resultant $H_2$ will assist in dehydration of $CH_3OH$ to BTEX.

3) $CH_4$ will activate to CHx and —H moieties. The —H moieties will help dehydration of oxygenates. CHx moieties will directly couple with the oxygen deficient site of the methanol and propagate to BTEX.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Klass, D. L. (1998) *Biomass for renewable energy, fuels and chemicals*, Academic Press, San Diego.
2. Elliott, D. C. et al. (1991) Developments in direct thermochemical liquefaction of biomass: 1983-1990, *Energy Fuels* 5, 399-410.
3. Chen, N. Y. and Koenig, L. R. "Process for converting cellulosic materials to hydrocarbon products," U.S. Pat. No. 4,933,283 (published Jun. 12, 1990).
4. Chen, N. Y. and Koenig, L. R. "Conversion of carbohydrates," U.S. Pat. No. 4,549,031 (published Oct. 22, 1985).
5. Chou, T.-s. and Melconian, M. G. "Heat balanced paraffin upgrading with co-fed oxygenate," U.S. Pat. No. 5,019, 663 (published May 28, 1991).
6. Lubango, L. M. and Scurrell, M. S. (2002) Light alkanes aromatization to BTX over Zn-ZSM-5 catalysts—Enhancements in BTX selectivity by means of a second transition metal ion, *Applied Catalysis A: General* 235, 265-272.
7. Horne, P. A. and Williams, P. T. (1996) Upgrading of biomass-derived pyrolytic vapours over zeolite ZSM-5 catalyst: effect of catalyst dilution on product yields, *Fuel* 75, 1043-1050.
8. Petrus, L. and Noordermeer, M. A. (2007) Biomass to Biofuels, a Chemical Perspective, *Green Chem.* 8, 861-867.
9. Corma, A. et al. (2007) Processing biomass-derived oxygenates in the oil refinery: Catalytic cracking (FCC) reaction pathways and role of catalyst, *J. Catal.* 247, 307-327.
10. Bridgwater, A. V. (1996) Production of high grade fuels and chemicals from catalytic pyrolysis of biomass, *Catal. Today* 29, 285-295.
11. Butter, S. A., Jurewicz, A. T., and Kaeding, W. W. "Conversion of alcohols, mercaptans, sulfides, halides and/or amines," U.S. Pat. No. 3,894,107 (published Jul. 8, 1975).
12. van Santen, R. A. (1991) Chemical basis of metal catalyst promotion, *Surf Sci.* 251-252, 6-11.

13. Li, W.-Y., Feng, J., and Xie, K.-C. (1998) Ni/ZSM-5 Catalyst for $CH_4$ Reforming with $CO_2$, *Pet. Sci. Technol.* 16, 539-553.
14. Noyori, R., Yamakawa, M., and Hashiguchi, S. (2001) Metal-Ligand Bifunctional Catalysis: A Nonclassical Mechanism for Asymmetric Hydrogen Transfer between Alcohols and Carbonyl Compounds, *The Journal of Organic Chemistry* 66, 7931-7944.
15. Gao, L. and Seegopaul, P. "Method of forming molybdenum carbide catalyst," U.S. Pat. No. 6,207,609 (published Mar. 27, 2001).
16. Shirazi, L., Jamshidi, E., and Ghasemi, M. R. (2008) The effect of Si/Al ratio of ZSM-5 zeolite on its morphology, acidity and crystal size, *Cryst. Res. Technol.* 43, 1300-1306.
17. Carlson, T. R., Jae, J., and Huber, G. W. (2009) Mechanistic Insights from Isotopic Studies of Glucose Conversion to Aromatics Over ZSM-5, *ChemCatChem* 1, 107-110.
18. Iliuta, M. C. et al. (2002) Methane Nonoxidative Aromatization over Ru-Mo/HZSM-5 in a Membrane Catalytic Reactor, *Ind. Eng. Chem. Res.* 41, 2371-2378.
19. Zheng, L. et al. (2006) Non-Oxidative Aromatization of $CH_4$-$C_3H_8$ over La-Promoted Zn/HZSM-5 Catalysts, *J. Nat. Gas Chem.* 15, 52-57.
20. Wang, L. et al. (1995) Activation and aromatization of methane and ethane over Mo(VI)/HZSM-5 and W(VI)/HZSM-5 zeolites catalysts, in *Studies in Surface Science and Catalysis* (H. K. Beyer, H. G. K. I. K., and Nagy, J. B., Eds.), pp 495-500, Elsevier.
21. Sily, P. D., Noronha, F. B., and Passos, F. B. (2006) Methane direct conversion on Mo/ZSM-5 catalysts modified by Pd and Ru, Journal of Natural Gas Chemistry 15, 82-86.
22. Ismagilov, Z. R., Matus, E. V., and L. T. Tsikoza. (2008) Direct conversion of methane on Mo/ZSM-5 catalyst to produce benzene and hydrogen: achievements and perspective, *Energy and Environment Science* 1, 526-541.

The invention claimed is:

1. A method for deoxygenating oxygenates, comprising:
   a) providing the following consisting of:
      i) a short chained hydrocarbon consisting of $C_1$-$C_4$ carbon atoms;
      ii) an alkali or transition metal impregnated ZSM-5 catalyst; and
      iii) a biomass comprising an oxygenate, wherein said oxygenate is glucose; and
   b) reacting said hydrocarbon with said oxygenate in the presence of said catalyst so as to create a reaction coupling hydrocarbon steam reforming and dehydrative aromatization to produce a deoxygenated hydrocarbon, wherein said deoxygenated hydrocarbon is an aromatic hydrocarbon comprising benzene, toluene, ethyl benzene, or xylenes.

2. The method of claim 1, wherein said hydrocarbon steam reforming and dehydrative aromatization reactions are concurrent.

3. The method of claim 1, wherein said short chained hydrocarbon is methane.

4. The method of claim 1, wherein said short chained hydrocarbon is derived from natural gas.

5. The method of claim 1, wherein said oxygenate is derived from thermal processing of biomass.

6. The method of claim 1, wherein said metal impregnated ZSM-5 catalyst is impregnated with nickel.

7. The method of claim 1, wherein said metal impregnated ZSM-5 catalyst is impregnated with platinum.

8. The method of claim 1, wherein said reaction generates molecular hydrogen.

9. The method of claim 8, wherein said hydrogen reacts with said oxygenates so as to aromatize said oxygenates, thereby removing oxygen in the form of water.

* * * * *